United States Patent [19]
Purtle

[11] Patent Number: 6,157,028
[45] Date of Patent: Dec. 5, 2000

[54] METHOD FOR DOSE MAPPING TO ENSURE PROPER AMOUNTS OF GAMMA IRRADIATION

[75] Inventor: Douglas R. Purtle, Overland Park, Kans.

[73] Assignee: JRH Biosciences, Inc., Lenexa, Kans.

[21] Appl. No.: 09/085,724

[22] Filed: May 28, 1998

[51] Int. Cl.$^7$ ...................................................... G01T 1/00
[52] U.S. Cl. ..................................... 250/252.1; 250/580
[58] Field of Search ................................. 250/252.1, 580, 250/473.1

[56] References Cited

U.S. PATENT DOCUMENTS

| | | | |
|---|---|---|---|
| 4,331,021 | 5/1982 | Lopez et al. | 73/1.86 |
| 4,663,772 | 5/1987 | Mattson et al. | 378/18 |

OTHER PUBLICATIONS

Note for Guidance: Good Manufacturing Practice for Medicinal Products: Use of ionizing radiation in the manufacture of medicinal products Annex 12, "Guide to good manufacturing practice for medicinal products", Directive 91/356. EEC, Jun. 13, 1991.

"Dose determination by Monte Carlo—a useful tool in gamma radiation process", C. Oliveira, J. Salgado, M. Luisa Botelho, L.M. Ferreira, Radiation Physics and Chemistry 57 (2000), p. 667–670.

H. Levine et al., "Temperature and Humidity Effects on the Gamma–Ray Response and Stability of Plastic and Dyed Plastic Dosimeters," *Radiat. Phys. Chem.*, vol. 14, 1979, pp. 551–574.

M.C. Saylor et al., "A Thin Film Recording Medium for Use in Food Irradiation," *Radiat. Phys. Chem.*, vol. 31, Nos. 4–6, 1988, pp. 529–536.

S. Biramontri et al., "Effect of Low Irradiation Temperature on the Gamma–Ray Response of Dyed and Undyed PMMA Dosimeters," *Radiat. Phys. Chem.*, vol. 48, No. 1, 1996, pp. 105–109.

*Primary Examiner*—Constantine Hannaher
*Assistant Examiner*—Albert Gagliardi
*Attorney, Agent, or Firm*—Michael B. Hurd; Shook, Hardy & Bacon L.L.P.

[57] ABSTRACT

A method of dose mapping that simulates actual product irradiation conditions utilizing a semisolid to fix dosimeter (18) inside product containers (14) and a dry ice substitute (16) to mimic the density of dry ice. The method comprising the steps of fixing dosimeter (18) in a semisolid mixture inside product containers (14) packed with a dry ice substitute (16) and irradiating. The results are then calculated and analyzed to produce an accurate dose map.

19 Claims, 1 Drawing Sheet

U.S. Patent Dec. 5, 2000 6,157,028
*Fig.1.*
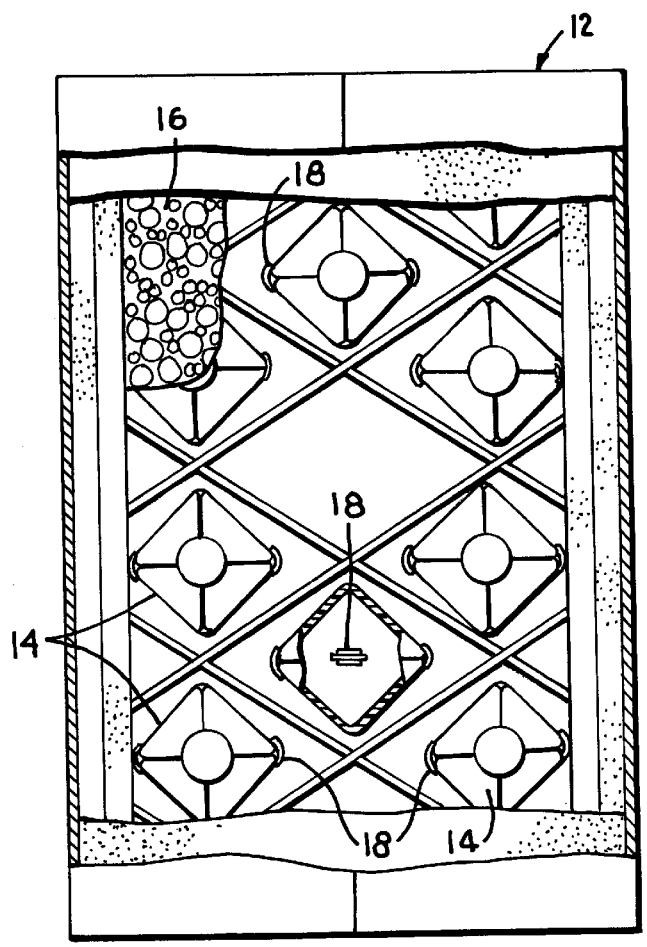
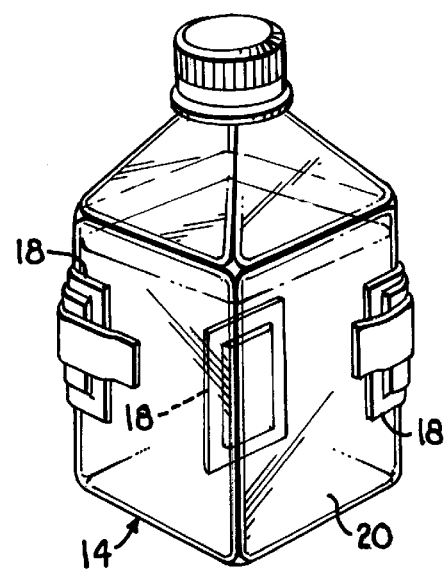
*Fig.2.*
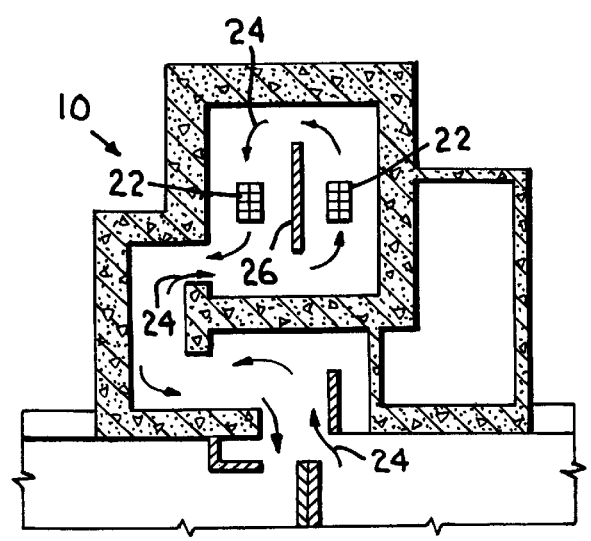
*Fig.3.*

METHOD FOR DOSE MAPPING TO ENSURE PROPER AMOUNTS OF GAMMA IRRADIATION

STATEMENT REGARDING FEDERALLY-SPONSORED RESEARCH OR DEVELOPMENT

Not applicable.

CROSS REFERENCE TO RELATED APPLICATIONS

Not applicable.

BACKGROUND OF THE INVENTION

This invention relates generally to a method for gamma irradiating products in a consistent reproducible manner to eliminate potential biological contaminants while maintaining biological activity, and specifically to a method which allows for a precise mapping of the dosage of gamma radiation delivered to the product throughout the carrier. Dose maps provide the manufacturers of biological material the information required to ensure that each of the product containers in a carrier receives an amount of radiation that falls within an acceptable range.

Biological products have validated specifications for inactivation treatment by gamma radiation. These biological products must be irradiated on dry ice in polyfoam containers to protect the product integrity. The polyfoam container insulates the product and the dry ice while maintaining temperatures at or below the validated specified range. Considerable amounts of energy and thus heat are generated during the irradiation process, temperatures typically exceed 10° C. to 15° C. above ambient. This temperature range is deleterious to the biological product.

Additionally, the bottle/product container configuration within the box significantly affects the amount of radiation penetration to the actual product. The greater the density, the lower the amount of penetration or delivered dose. It is the irradiation received at each point that allows for inactivation of bacteria, fungi, mycoplasma, bacteriophage and viral contaminants. Therefore, specific validated bottle configurations have been determined to maximize radiation penetration to all bottles within the polyfoam containers. These configurations enable a more uniform distribution of radiation, thus reducing the minimum to maximum radiation dose throughout the product. An additional factor to consider is placement of the shipping boxes on carriers. Carriers are used to bring the shipping boxes to the radiation source. These irradiation conditions must be emulated in the dose mapping procedures.

Dose mapping is a method whereby manufacturers of biological products are able to predetermine an amount of radioactivity received at a specific point in a carrier. New dose maps are required each time an irradiation parameter is changed. For example, each time the box, i.e., box configuration, bottle type, carrier configuration, or the source of radiation is changed, a new dose map is required. These dose maps are performed on product irradiation models that emulate irradiation conditions without using a product in the system. In these systems it is of vital importance that all parameters are identical to actual product irradiation conditions. If all the parameters, such as density and product positioning, are not identical to product irradiation conditions, the dose map will not be an effective way to establish a protocol whereby each product container receives an amount of radiation that falls into a specific range. This range is important because if the amount of radiation received is below a predetermined amount there would be inadequate inactivation of adventitious agents and if the amount of radiation received is above a predetermined amount, the product will lose biological activity.

There is one main reason why dose mapping is not done on actual product. Dosimeters, which are used to measure the amount of radioactivity, do not give accurate data in cold conditions, less than −20° C. Since the dosimeters cannot be used in cold conditions, any product used would be destroyed. Thus it would be a waste of resources to use product for dose mapping. Therefore, a method is needed whereby manufacturers of biological materials are able to determine the amount of radiation at a specific point in an irradiation model designed to emulate product irradiation conditions. The closer the test conditions are to actual irradiation conditions, the more precise the dose mapping will be, thus allowing a proper range of radioactivity to be delivered to each product container.

The reason dosimeters do not give proper readings in cold conditions is because the kinetics of the chemical reaction are enhanced which would ultimately lead to under exposure of the product and incomplete inactivation. During irradiation dry ice is used to maintain the integrity of the product. Therefore, to emulate product irradiation conditions, a dry ice substitute is required for dose mapping experiments. A dry ice substitute requires approximately the same shape and density as dry ice so that the same amount of radioactivity reaches the dosimeters in the dose map system as would under product irradiation conditions. Dry ice pellets have a density of approximately 0.785 g/ml.

One known substitute for dry ice includes the use of dog food with salt pellets combined in a ratio of 5.2 pounds of dog food with 4.8 pounds of salt pellets. Dog food has a density of 0.4596 g/ml. Therefore, one problem with dog food is that it does not have a density similar to dry ice. In addition to the density, the dog food has a shape different from dry ice. Dry ice is $1\frac{3}{8} \times \frac{3}{4} \times \frac{1}{2}$" and the dog food is $\frac{5}{8} \times \frac{5}{8} \times \frac{3}{8}$". Therefore, the density and shape of dog food made it an inadequate substitute. Additionally, dog food was too brittle for repeated use which increased the cost of dose mapping. Therefore, there is a need for a dry ice substitute that more closely emulates dry ice and that does not lose its shape over time.

In addition to the need for an effective dry ice substitute, dose map systems would be more effective if the dosimeters could be fixed into the center of the product container so that an accurate reading at the exact center of the product container could be recorded. Biological product or other liquids are not effective for dose mapping for several reasons. For example, a liquid will not fix the dosimeter into a center position. In a liquid, the dosimeter will float around making an accurate reading of the exact center of the product impossible. Another reason for needing an improved medium is that current mediums (saline solution) do not have a density similar to the product, thereby reducing the chance of obtaining a true dose map. Lastly, fiscal responsibility requires the use of a cheap and effective product substitute.

One product that manufacturers currently expose to radiation is animal serum. Animal serum and animal proteins derived from serum are essential supplements required for the growth of most cells in vitro. Serum is indispensable in the production of biologicals for animal and human pharmaceutical markets. It has the encumbrance of possible contamination by adventitious agents. At best, this leaves pharmaceutical manufacturers open to failed production runs and, at worst, introduction of a viral contaminant in the final product.

In addition to quality control, appropriate testing of all animal-derived raw materials is required in the manufacture of pharmaceuticals. The Code of Federal Regulations, Title 9,§113.53, requires the testing of serum products by serial passage in susceptible cell lines for the determination of viral contamination. This test is inadequate for detecting low levels of contamination in serum products. Typically, most production scale lots of serum are 1,000 liters. A 45 ml sample of serum is generally all that is required for Title 9 testing. Assuming a viral titer of one viable particle per liter of serum, the chance of obtaining a contaminated particle in any test sample is less than four percent (4%).

Currently, several manufacturers are utilizing gamma radiation as a treatment for potential contamination. Gamma radiation is the preferred treatment method due to its effective inactivation, lack of residuals, lower lot-to-lot variation, and it is minimally intrusive. Although, currently it is difficult to map the exact amount of radiation received at any particular point in the carrier, due to the high density of the product along with void spaces between the product container, it is impossible to guarantee the specified delivered dose without knowing the precise amount of radiation being received at these individual places inside a carrier. The density variation makes it possible to have portions of the product receive too much radiation and other portions not receive adequate amounts of radiation. The former possibly degrading the biological material, and the latter allowing possible contamination due to ineffective inactivation of adventitious agents.

Thus, current techniques for measuring the amount of radiation at a specific point in a carrier are inadequate to allow a realistic dose map to be created. For example, current techniques do not allow a proper determination of the amount of radiation received at the very center of a product container. Even if a dosimeter could be fixed to the center of a container, the density will not be the same as when product is in the container. Thus, current systems will not emulate actual irradiation conditions. Additionally, the current dry ice substitute lacks the proper parameters to emulate dry ice effectively. Therefore, a method is needed whereby dosimeters can be fixed to the center of a product container, product containers are filled with a material having a density similar to that of the product to be irradiated, and an effective dry ice substitute placed in the shipping box to eliminate void spaces between the product containers and the shipping box.

The above method is needed to comprehensively dose map carriers to ensure that all areas of the carriers receive a dose of radiation within a specified range, such that there is significant contaminant reduction without compromising product performance.

SUMMARY OF THE INVENTION

It is an object of the present invention to provide a method for dose mapping whereby a comprehensive dose map can be performed to ensure that all areas of a carrier receive a dose of gamma radiation within a specific range, such that levels of radiation produce significant viral reduction without compromising product performance.

An additional object of the invention is to provide a cheap product substitute of equivalent density that also provides the advantage of fixing a dosimeter in a centrally located position within the product container.

Another object of the invention is to provide a method whereby the amount of gamma radiation can be determined at a specific point in a carrier.

Therefore, one embodiment of the present invention is drawn to a method of dose mapping an amount of radiation received at specific points within the irradiation model which emulates actual product irradiation conditions comprising the steps of fixing a dosimeter in a solidified agar mixture inside a product container, packing a dry ice substitute around the product container, irradiating the irradiation model and analyzing the dosimeter data.

Several advantages are realized by utilizing the methods of the present invention. One advantage is the creation of a more accurate dose map which allows for a higher quality product because there is less chance of the product being over-irradiated which causes biological degradation or under-irradiated which leaves possible contaminants.

Additional objects, advantages, and novel features of the invention will be set forth in part in a description which follows, and in part will become apparent to those skilled in the art upon examination of the following, or may be learned by practice of the invention.

BRIEF DESCRIPTION OF THE DRAWING

In the accompanying figures, which form part of this specification and are to be read in conjunction therewith, and in which like-reference numerals are used to indicate like parts in the various views:

FIG. 1 illustrates a top view of a shipping box containing dry ice substitute and product containers;

FIG. 2 illustrates a perspective view of a product container containing agar with dosimeters placed in the center of the agar and on the sides of the container; and FIG. 3 illustrates the layout of the facility used for irradiating samples.

DETAILED DESCRIPTION OF THE INVENTION

Referring to the drawing in greater detail and initially to FIGS. 1 and 2, a shipping box 12 is used to hold product containers 14 and dry ice substitute 16. Dosimeters 18 are placed on the product containers and inside the product containers. The dosimeters are fixed in the center of product containers 14 by agar 20 and taped to the sides of the product containers.

Shipping boxes 12, as seen in FIGS. 1 and 2, are used to hold product containers 14 and dry ice substitute 16. Shipping box 12 can be formed of any rigid material which will hold the product containers and the dry ice substitute. In the preferred embodiment, the shipping boxes are made of polyfoam.

The product containers 14 are used to hold the agar 20. Dosimeters 18 are taped to the outside of the product containers 14 in addition to being fixed in a center position inside the product containers. The product containers must be the same containers used to hold actual product.

Dry ice substitute 16 is used as a substitute for dry ice in shipping box 12. The dry ice substitute can be made of anything having a shape and density similar to dry ice. Dry ice is solid carbon dioxide. The dry ice used has a shape of 1⅜×¾×½ inch and a density of 0.785 g/ml. The dry ice substitute comprises dried animal food and salt pellets. The dried animal food has a density of 0.642 g/ml with a shape of 1⅜×⅝×½ inch. The salt pellets have a density of 1.102 g/ml and a shape of 1–⅙×⅝×⅜ inch. These two components are combined in a ratio of seven parts dried animal food with three parts salt pellets to yield an average density that is equivalent to the average density of dry ice. In one embodiment the dried animal food is PURINA® Labdiet and the salt pellets are MORTON® system saver pellets, 99.5% pure salt. Additionally, the Labdiet is not brittle and lasts for many experiments, thus saving money. The dry ice substitute is then packed into shipping boxes and packed around the product containers.

Dosimeters 18 are used to determine the amount of radiation received at particular points in carrier 22. Dosimeters are taped to the outside of product containers 14. Additionally, dosimeters are inserted into product containers where they are fixed into a center position by agar 20. Dosimeters can be any type of device that can detect specific amounts of radiation and are small enough for use in the dose mapping system. In the preferred embodiment, the dosimeters are effective in a range of 5 to 50 kGy. The dosimeters are supplied by the irradiation facility.

Any semisolid substance can be used to fix dosimeter 18 in the approximate center of product container 14. In the preferred embodiment agar 20 is used as a product substitute to fix the dosimeter in the approximate center of the product container. Agar is a mucilaginous complex sulfated polymer of galactose units. The agar allows the dosimeters to be fixed approximately in the center of product containers 14. The agar further acts as a shield against the radiation source whereby the dosimeters receive an amount of radiation that would be approximately equal to the amount received during product irradiation. The agar must have a gel point less than 50° C. and a melting point greater than 85° C. The significance of these two points is that it allows for filling of plastic bottles with agar without melting the bottle. Additionally, the agar will remain a solid during irradiation. In the preferred embodiment, the agar preparation should have a density of approximately 1.2 kg/L which is approximately the density of frozen serum. The density of agar is variable depending on its preparation. In the preferred embodiment, the agar is prepared by autoclaving 15 liters of water with 250 grams of agar mixed in with the water.

FIG. 3 illustrates the general floor plan 10 of the radiation facility. Shipping boxes 12 are packed with product containers 14 containing agar 20. Dosimeters 18 are taped to the product containers and inserted into the center of the product containers where they are fixed into position by the agar. The shipping boxes are then packed with a dry ice substitute 16 and placed onto a carrier 22. The carrier holds seven to fifteen shipping boxes, depending on the size of the box. The carrier is attached to a conveyor system 24. The conveyor system brings the carrier into a room containing a gamma radiation source 26.

Carrier 22 can be any device which will hold a number of shipping boxes 12. The carrier is a metal structure capable of carrying several shipping boxes. In the preferred embodiment, the carrier holds seven to fifteen shipping boxes.

Conveyor system 24 is used to transport carriers 22 to the radiation source 26. The conveyor system can be any means by which the carriers are brought to and from the radiation source 26. In the preferred embodiment, the conveyor system brings a carrier to the radiation source in an orientation where a first side of the shipping boxes receives radioactivity on the first pass of the radiation source, then the conveyor system brings the carrier by the radiation source a second time in an orientation where a second, opposite, side of shipping boxes receives radioactivity. The conveyor system moves the carriers to one of eleven positions. The conveyor system has a means for varying the time at which the carriers are held at each of the eleven positions. Each carrier is held at each position for a specified time. This means is used to control the length of exposure to the radiation source and to reduce variability in exposure.

Radiation source 26 is any source of radiation. In the preferred embodiment, the radiation source produces gamma radiation from Cobalt 60.

Generally, product containers 14 are filled with Agar 20. The agar is prepared by mixing the agar with water and then autoclaving. In the preferred embodiment, the agar is prepared by mixing 250 grams of agar with 15 liters of water and then autoclaving. After the agar mixture is removed from the autoclave it is a hot liquid. This liquid is allowed to cool and then poured into product containers, and it is further allowed to cool to room temperature. At room temperature the agar is a semisolid gel. Additionally, the agar remains a semisolid during the irradiation process.

Dosimeters 18 are then taped to the outside of the product containers 14. They are taped onto the product containers with SCOTCH® tape. Each product container has a dosimeter 18 taped on a first side and a second opposite side as seen in FIG. 2. Dosimeters are then fixed into the center of the product container. Covers are then placed onto the product containers.

Product containers 14 are placed into shipping boxes 12. The configurations of the product containers will be identical to actual irradiation conditions. An amount of dry ice substitute 16 equal to the amount of dry ice that would be present at the time of irradiation is then packed into the shipping boxes. In the preferred embodiment, ten pounds of dry ice substitute 16 is packed into the shipping boxes. The shipping boxes are then sealed shut with tape.

Shipping boxes 12 are then stacked onto carriers 22. Carriers 22 will hold up to 15 shipping boxes. A space is placed on the bottom of the carrier to elevate the shipping boxes. This space allows an accurate and consistent amount of radiation to reach the product containers. The amount of space is determined by evaluation of the non-product dose map data obtained from the irradiation facility.

Carriers 22 with shipping boxes 12 are then sent by conveyer system 24 to the radiation source 26. The radiation source is contained in a separate radiation room. After exposure to radiation source, the carriers are returned on the conveyer system.

After the radiation treatment the dosimeters 18 are collected and analyzed to create a dose map which can be used to ensure that each of the product containers 14 receive the proper amount of radiation.

The preferred embodiment is set out in Example I.

EXAMPLE I

Agar 20 was prepared by adding fourteen liters of tap water to a twenty liter capacity glass carboy. The water was rapidly mixed with a magnetic stir bar. 250.0 grams of agar was weighed out and slowly added to the carboy. The carboy opening was loosely covered with aluminum foil. The solution was allowed to mix for thirty minutes. The solution was then brought to fifteen liters with tap water. The solution was mixed for an additional thirty minutes. The solution was autoclaved at 121° C. for forty-five minutes. More than one carboy may be autoclaved at once. After the agar cooled, but before it gelled, the 500 ml, 1000 ml and/or 4000 ml product containers 14 were filled to a level similar to the level of product usually found in the container. The liquid agar was poured using a funnel. Although, the agar could be transferred by a peristaltic pump and flexible tubing. The caps were loosely placed on the product containers while the agar solidified overnight at room temperature. The caps were tightened down once the agar 20 was solidified. This process was repeated until 140×500 ml, 112×1000 ml and 42 of each type of 4000 ml product containers were filled. The product containers of agar were stored at room temperature until needed.

Because delivered dose is directly dependent on density, mimicking the density of dry ice added to frozen products is essential for accurate dose mapping. For each of the 63 polyfoam shipping boxes 12 that were used, one bag containing ten pounds (4.53 kg) of dry ice substitute 16 was required. Ten pounds of dry ice substitute were made by mixing seven pounds Labdiet with three pounds salt pellets in a plastic bag. The top of the bag was twisted to keep the contents from escaping. The bags of dry ice substitute were stored in a cool, dry place until needed.

A cardboard divider was added to each of fourteen shipping boxes 12. Ten 500 ml product containers 14 of agar 20 were put into each of fourteen shipping boxes containing a divider. Eight 1000 ml product containers 14 of agar 20 were put into each of the fourteen shipping boxes (without dividers). Three 4000 ml Berlin product containers of agar were put into each of fourteen shipping boxes (without dividers). Three 4000 ml Medical and Veterinary Supply product containers of agar were put into each of 21 shipping boxes (without dividers). One bag (10 pounds) of dry ice substitute was added to each shipping box, the polyfoam lid was replaced, and sealed with packing tape.

The shipping boxes 12 were labeled with the appropriate product container 14 labels.

"500" for 500 ml product container;
"1000" for 1000 ml product container;
"4000 B" for 4000 ml supplier product container; or
"4000 M" for 4000 ml medical and veterinary supply product container.

The labels were affixed to all the cases. The shipping boxes 12 were placed on pallets, 27 shipping boxes per pallet. The shipping boxes were then shipped to the irradiation facility.

At the irradiation facility, the carrier 22 and carrier position (level) of each shipping box was labeled accordingly. Each carrier can hold seven shipping boxes, numbered 1 (bottom) through 7 (top). The "500" shipping boxes were in carriers 1 and 2, "1000" were in 3 and 4, "4000 B" were in 5 and 6, and the "4000 M" were in carriers 7, 8 and 9.

At the irradiation facility, each dosimeter 18 was labeled with a white label containing the eventual location of the dosimeters within its shipping box 12. Included were the shipping box location (carrier 22 and level) plus a letter corresponding to the dosimeter map FIG. 2. Each shipping box was opened and the bag of dry ice substitute 16 was removed. Using FIG. 2 as a guide, the dosimeters were attached on the outside of the bottles using SCOTCH® tape or equivalent. The dosimeters were laid as flat as possible against the bottle and positioned approximately in the middle of the product/agar, which is lower than the exact middle of the product container 14 itself. The dosimeters on the 500 ml product containers 14 were placed on the vertical edge of these product containers because of their orientation within the shipping box 12. The cap was removed and the dosimeters were placed in the positions shown in FIG. 2. Using a long pair of forceps, the dosimeters were submerged and fixed into the middle of the agar. The product container was recapped and placed into the shipping box in the proper configuration. One bag of dry ice substitute was emptied into each shipping box case and evenly distributed around the product containers. The lid was replaced and the shipping box was sealed with packaging tape. The shipping boxes were raised off the bottom of the carriers by foam sheets. The height that the shipping boxes were raised was determined from the initial dose map performed by personnel at the irradiation plant after each cobalt source reloading. Different product container sizes must be evaluated separately, i.e., shipping boxes of 1000 ml product containers 14 need to be 5 raised higher than shipping boxes of 500 ml product containers. This spacing reduced the minimum to maximum range and assured that all product containers fell within the specified exposure range of 25–35 kGy.

The shipping boxes 12 were irradiated as specified. It was requested that the 0C1 position receive a target dose between 25–35 kGy, although for dose mapping purposes, the dosage range is not crucial. The 0C1 position is a designation for a specific portion of carrier 22. These designations correspond to a map created by the irradiation facility. The maps allow for the identification of specific portions with in the carrier. Once the shipping boxes 12 were unloaded, and the lids removed, the dosimeters were collected by removing the tape or recovering from the agar with forceps. The dosimeters were combined from each shipping box 12 separately with rubber bands and turned over for analysis. The dry ice substitute 16 was poured back into bags for future use.

The dosimeter data was used to find the 0C1 values for each of the two carriers 22 of 500 ml product containers 14 and a mean value ($0C1500_{\bar{x}}$) was computed. The minimum and maximum delivered dosages for both carriers of 500 ml product containers was found. The minimum correction factor for 500 ml bottles (CFMin500) was computed by dividing Min500 by $0C1500_{\bar{x}}$. For example, if the minimum delivered dosage at any dosimeter 18 was 25.1 kGy and the average 0C1 reading was 28.7 kGy, then CFMin500=25.1/28.7=0.875. Next, the maximum correction factor for 500 ml product containers (CFMax500) was computed by dividing Max500 by $0C1500_{\bar{x}}$. For example, if the maximum delivered dosage at any dosimeter was 30.3 kGy and the average 0C1 reading was 28.7 kGy, Then CFMax500=30.3/28.7=1.056. These steps were repeated for all other product containers tested.

The computed correction factors for each product container 14 size/configuration were used every time a target dose range was given to irradiating personnel while the same cobalt source was in use. The minimum target dosage level was computed by dividing the low end of the acceptable dosage range by the CFMin500. For instance, if the acceptable range is 25–35 kGy and CFMin is 0.875, then the new low end target dosage for the 0C1 position for 500 ml bottles is 25/0.875=28.6 kGy. Next the maximum target dosage level was computed by dividing the high end of the acceptable dosage range by the CFMax500. For instance, if the acceptable range is 25–35 kGy and CFMax500 is 1.056, then the high target dosage for the 0C1 position for 500 ml bottles is 35/1.056=33.1 kGy. Thus, using these numbers, a desired dosage range for serum in 500 ml product containers is 25–35 kGy; therefore, 28.6–33.1 kGy needs to be delivered to the 0C1 position. Thus, if the dosimeter record for this hypothetical run showed all 0C1 delivered dosage from all carriers to be between 28.6 and 33.1 kGy, than all product containers containing product were known to have actually received dosages within the desired 25–35 kGy range.

From the foregoing, it will be seen that this invention is one well adapted to attain all the ends and objects hereinabove set forth together with other advantages which are obvious and which are inherent to the invention. It will be understood that certain features and subcombinations are of utility and may be employed without reference to other features and subcombinations. The above examples discussed the techniques and procedures used in the current invention, and it is understood that there are many other techniques and procedures that could be employed that would allow an individual of ordinary skill in the art to perform the claimed invention and that these other techniques and procedures are contemplated by and are within the scope of the claims. Since many possible embodiments may be made of the invention without departing form the scope thereof, it is to be understood that all matter herein set forth, and shown in the drawings arc to be interpreted as illustrative and not in a limiting sense.

I claim:

1. A method of dose mapping an amount of radiation received at specific points within an irradiation model which emulates irradiation conditions for a product having a predetermined density comprising the steps of:

fixing a dosimeter inside a product container;

packing a dry ice substitute around the product container;

irradiating the irradiation model; and analyzing the dosimeter.

2. A method of dose mapping as claimed in claim 1 wherein the product container is filled with a semisolid.

3. A method of dose mapping as claimed in claim 2 wherein the semisolid is agar.

4. A method of dose mapping as claimed in claim 3 wherein the agar mixture has a density substantially equal to the product.

5. A method of dose mapping as claimed in claim 1 wherein the dry ice substitute has an equivalent shape and density of dry ice.

6. A method of dose mapping as claimed in claim 5 wherein the dry ice substitute is a combination of dry animal food and salt pellets.

7. A method of dose mapping as claimed in claim 6 wherein the dry ice substitute is formed with 7 parts dry animal food and 3 parts salt pellets.

8. A method of dose mapping which emulates irradiation conditions comprising the steps of:

fixing a dosimeter in an agar mixture inside a product container inside a shipping box, the agar mixture being prepared to a specific density;

packing the shipping box with a dry ice substitute;

irradiating a plurality of shipping boxes positioned inside a carrier; and analyzing the dosimeters.

9. A method of dose mapping as claimed in claim 8 wherein the agar mixture has a density substantially equal to a serum product.

10. A method for dose mapping as claimed in claim 9 wherein the agar is prepared by mixing 15 liters of water with 250 grams of agar and autoclaving.

11. A method of dose mapping as claimed in claim 8 wherein the dry ice substitute is a combination of dry animal food and salt pellets.

12. A method of dose mapping as claimed in claim 11 wherein the dry ice substitute is formed with 7 parts dry animal food and 3 parts salt pellets.

13. A method of dose mapping as claimed in claim 12 wherein the dry ice substitute has a shape and density equivalent to dry ice.

14. A method of dose mapping an amount of radiation received at specific points within an irradiation model which emulates product irradiation conditions comprising the steps of:

filling product containers with an agar mixture;

placing dosimeters on the product containers and fixing dosimeters inside the product containers by pushing the dosimeters into the agar mixture;

placing the product containers into shipping boxes;

packing a dry ice substitute around the product containers and scaling the shipping boxes;

placing the shipping boxes in carriers;

irradiating the carriers; and analyzing the dosimeters.

15. A method of dose mapping as claimed in claim 14 wherein the dry ice substitute has a density equivalent to dry ice.

16. A method of dose mapping as claimed in claim 15 wherein the dry ice substitute is a combination of dry animal food and salt pellets.

17. A method of dose mapping as claimed in claim 16 wherein the dry ice substitute is formed with 7 parts dry animal food and 3 parts salt pellets.

18. A method of dose mapping as claimed in claim 14 wherein the agar mixture has a density substantially equal to a serum product.

19. The method of claim 18 wherein the agar is formed by mixing 250 grams of agar with 15 liters of water and autoclaving.

* * * * *